United States Patent
Locatelli et al.

(12)

(10) Patent No.: US 7,029,843 B1
(45) Date of Patent: Apr. 18, 2006

(54) METHOD FOR THE QUANTITATIVE DETECTION OF NUCLEIC ACIDS

(75) Inventors: Giuseppe Locatelli, Milan (IT); Paolo Lusso, Milan (IT); Mauro Malnati, Milan (IT); Francesca Salvatori, Milan (IT); Gabriella Scarlatti, Milan (IT)

(73) Assignee: Fondazione Centro San Raffaele Del Monte Tabor, Milan (IT)

( * ) Notice: Subject to any disclaimer, the term of this patent is extended or adjusted under 35 U.S.C. 154(b) by 0 days.

(21) Appl. No.: 09/831,820

(22) PCT Filed: Nov. 17, 1999

(86) PCT No.: PCT/EP99/08847

§ 371 (c)(1),
(2), (4) Date: Jun. 5, 2001

(87) PCT Pub. No.: WO00/29613

PCT Pub. Date: May 25, 2000

(30) Foreign Application Priority Data

Nov. 17, 1998 (IT) .......................................... MI98A2491

(51) Int. Cl.
*C12Q 1/68* (2006.01)
*C12P 19/34* (2006.01)
*C07H 21/02* (2006.01)

(52) U.S. Cl. .............................. 435/6; 435/5; 435/91.2; 536/22.1; 536/23.1; 536/24.3; 536/24.31

(58) Field of Classification Search .................... 435/6, 435/91.2, 5; 536/22.1, 23.1, 24.3, 24.31
See application file for complete search history.

(56) References Cited

U.S. PATENT DOCUMENTS 6,395,470 B1 * 5/2002 WalkerPeach et al. ......... 435/5

FOREIGN PATENT DOCUMENTS

EP 0 623 682 11/1994
WO WO95/34684 12/1995

OTHER PUBLICATIONS

Kennedy et al, "HHV8 and female kaposi's sarcoma", J. Pathol. (1997) 183:447–452.*

Gibson U. E. M. et al.: "A Novel Method for Real Time Quantitative RT–PCR" Genome Research, US, Cold Spring Harbor Laboratory Press, vol. 6, No. 10, Oct. 1996, pp. 995–1001.

Woudenberg T. M. et al.: "Quantitative PCR by Real Time Detection" Proceedings Of The SPIE, vol. 2680, Jan. 1996.

Secchiero P. et al.: "Quantitative PCR for Human Herpesviruses 6 and 7" Journal Of Clinical Microbiology, US, Washington, DC, vol. 33, No. 8, Aug. 1995, pp. 2124–2130.

Kennedy M. M. et al.: "Identification of HHV8 in Early Kaposi's Sarcoma: Implications For Kaposi's Sarcoma Pathogenesis" Molecular Pathology, vol. 51, No. 1, Feb. 1998, pp. 14–20.

Zimmermann K. et al.: "Technical Aspects of Quantitative Competitive PCR" Biotechniques, US, Eaton Publishing, Natick, vol. 21, No. 2, Aug. 1996, pp. 268–270, 272, 27.

* cited by examiner

*Primary Examiner*—Jeffrey Fredman
(74) *Attorney, Agent, or Firm*—Nixon & Vanderhye

(57) ABSTRACT

Provided herein is a method for the quantitative detection of nucleic acids based on the use of a calibrator, suitable primers and probes, and a nucleic acid polymerase with 5'–3' nuclease activity.

7 Claims, 6 Drawing Sheets

Fig. 1

STANDARD PLASMID

A

Figure 2:
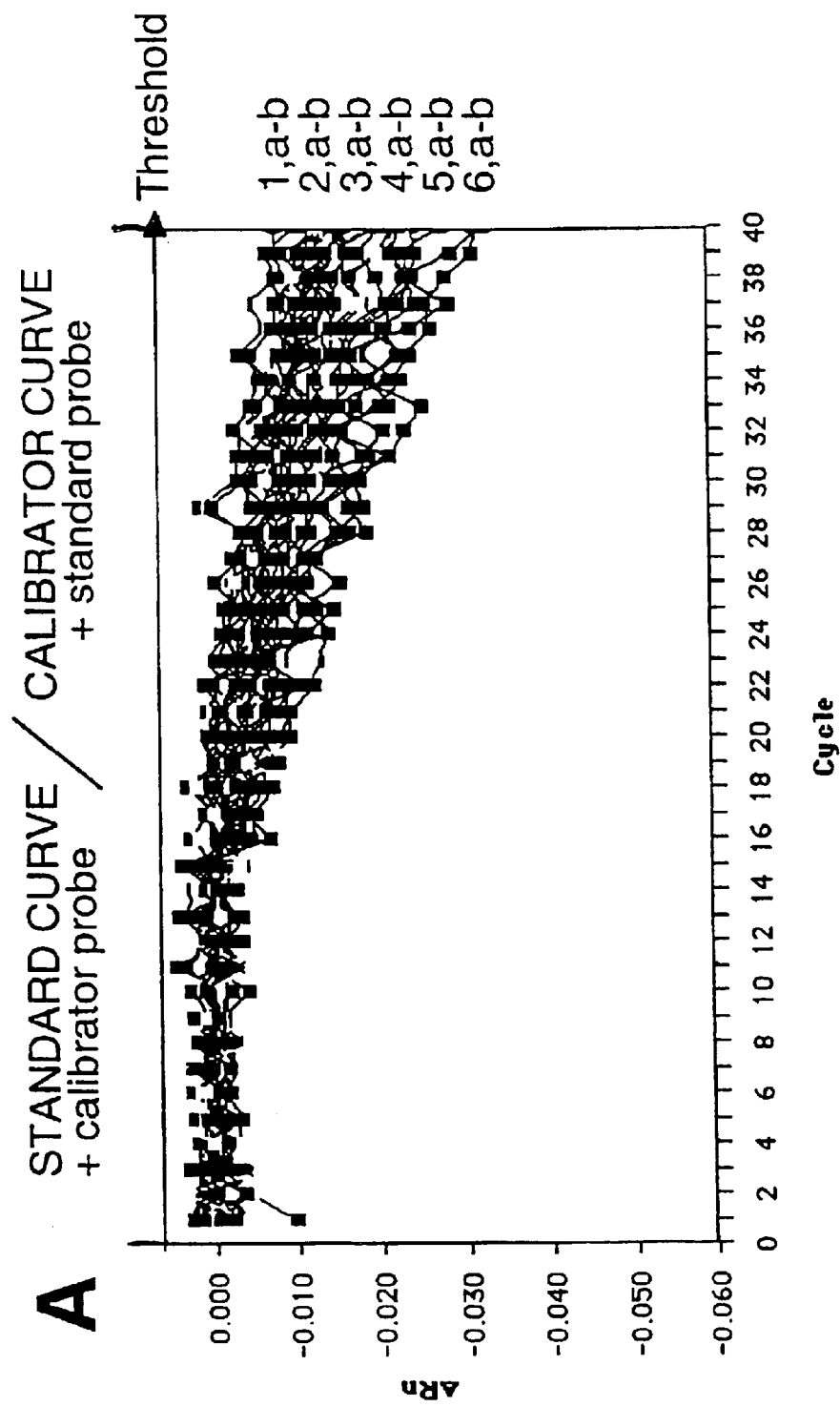
Figure 2:
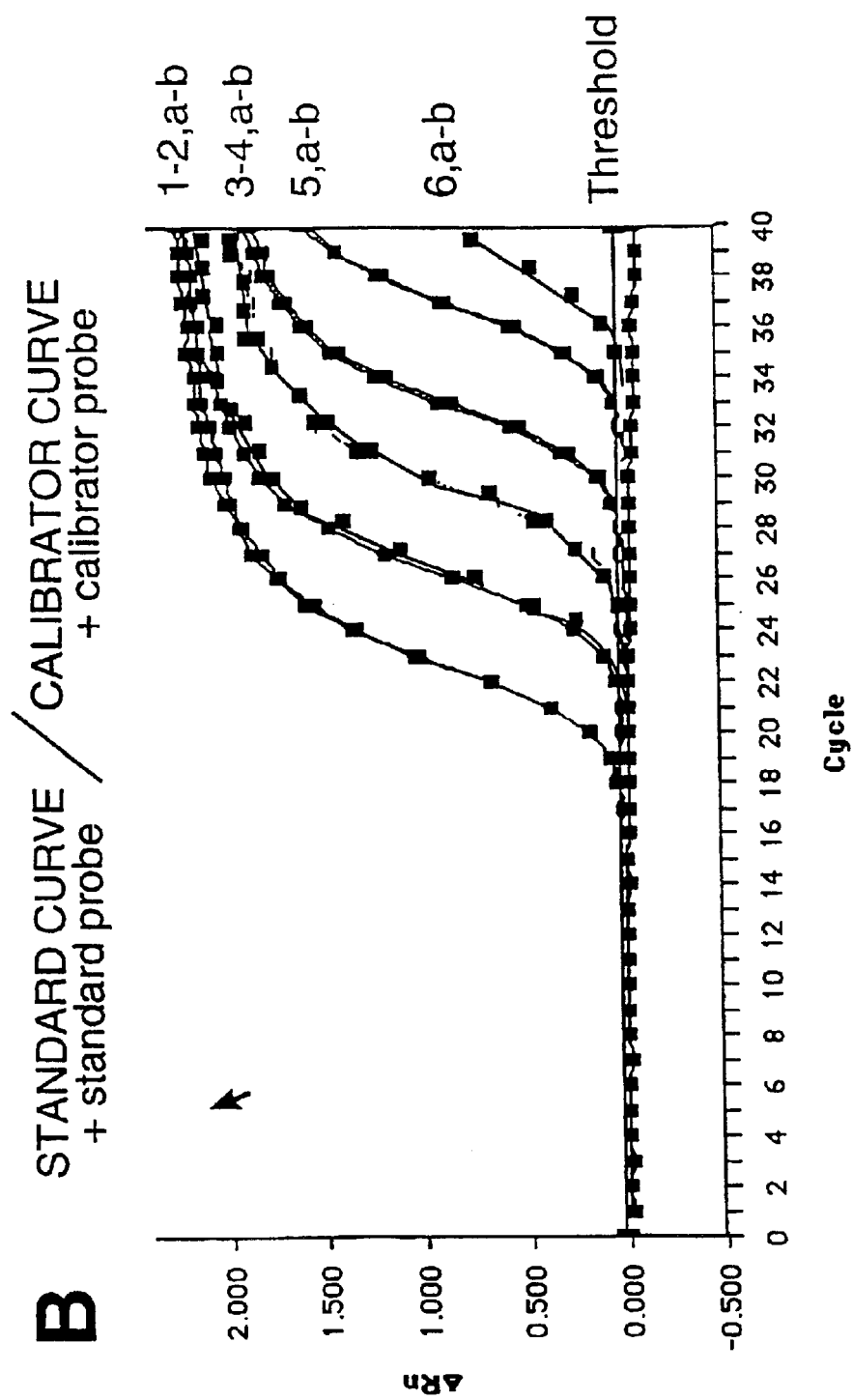

```
                                                                    400
CAAACGACAA AGCCAAATTA TCCAGAGCGG CATCGATATT TAACTTTGTT
GTTTGCTGTT TCGGTTTAAT AGGTCTCGCC GTAGCTATAA ATTGAAACAA

450
TTTTTTcac cagaacgtcac accgaagga atAACGCTCG TCACAAACAT
AAAAAAgtg gtctgcagtg tgggttcct tgTTGCGAGC AGTGTTTGTA 500
AAATTCTGT GTAGGCGTTT CGATCATCCT CAACCTAGCG CTCGGGGCTG
TTTTAAGACA CATCCGCAAA GCTAGTAGGA GTTGGATCGC GAGCCCCGAC
                                                               →
```

CALIBRATOR.

B

```
                                                                    400
CAAACGACAA AGCCAAATTA TCCAGAGCGG CATCGATATT TAACTTTGTT
GTTTGCTGTT TCGGTTTAAT AGGTCTCGCC GTAGCTATAA ATTGAAACAA

450
TTTTTTac gcaacgccaa cagacctagc gaAACGCTCG TCACAAACAT
AAAAAAatg cgttgcggtt gtctggatcg ctTTGCGAGC AGTGTTTGTA 500
AAATTCTGT GTAGGCGTTT CGATCATCCT CAACCTAGCG CTCGGGGCTG
TTTTAAGACA CATCCGCAAA GCTAGTAGGA GTTGGATCGC GAGCCCCGAC
                                                               →
```

METHOD FOR THE QUANTITATIVE DETECTION OF NUCLEIC ACIDS

The present application is a 371 U.S. National Phase of Application PCT/EP99/08847, filed 17 Nov. 1999.

The present invention relates to a method for quantitative detection of nucleic acids from a biological fluid sample.

The method of the invention may be suitably applied to diagnosis of viral and any other pathogenic agents and to monitor safety and/or genetic composition of waters, foods and plant species used in the alimentary field.

BACKGROUND ART

A commonly used strategy to detect the presence of pathogens, in biological fluids, is the detection of an antigen (direct method) or a respective antibody (indirect method). However, this strategy, performed with immunometric techniques such as ELISA, IFA or Western Blotting, is limited because of the scarce quantitation accuracy, precision and sensitivity, of the different antibody cross-reactivity and of the impossibility to obtain precocious diagnosis.

Another approach relies on the detection of nucleic acids specific for each kind of molecular target from any biological source, using the amplification by polymerase chain reaction (PCR). This technique, in its more sophisticated version i.e. the quantitative competitive PCR (qcPCR), makes it possible to reach a high sensitivity and a quite accurate quantitative measure, as well as to obtain a diagnosis a short time after contact between the patient and the pathogen. Nevertheless the precision and accuracy of this system is assured in a narrow quantitation range, thus forcing the operator to multiply the number of replies (typically 8) of the sample under investigation; furthermore a long time and additional costs for the amplified product detection steps are necessary.

The first systems that assessed PCR kinetics in real time were based on an intercalating substance such as ethidium bromide. This substance binds to the polymerizing double strand DNA proportionally, enhancing its fluorescence in response to UV excitation; the fluorescence emitted from the intercalated ethidium molecules was registered by a CCD camera in a thermal cycler equipped to irradiate the samples with UV rays and plotted against the amplification cycle number (Higuchi et al., Biotechnology 10:413–417). The main limitation of this technique is that the signal is generated also from the unspecific PCR products.

Subsequently the method known as TaqMan, described in U.S. Pat. No. 5,210,015 was introduced. This method is based on the real time detection of the fluorescence deriving from the degradation, directly dependent on the nascent PCR product, of a labeled probe specifically hybridizing to the segment to amplify, by means of the Taq polymerase enzyme. The PCR reaction mix contains a non-extendable oligonlucleotide probe, labeled with two fluorescent molecules, a reporter at the 5' end, and a quencher at the 3' end; the probe sequence must be complementary to a region of the DNA under investigation located between the two annealing sites of the oligonucleotide primers.

During the PCR amplification reaction, the Taq Polymerase enzyme specifically activated by the primers starts duplicating the DNA under investigation; when the enzyme contacts the probe annealed to the DNA, cuts it by its 5' nuclease activity, removing it and consequently separating the fluorescent molecules; the emission from the reporter fluorochrome becomes thus measurable and, each DNA molecule being accompanied by a reporter molecule release, the total fluorescence is at any time proportional to the amplified DNA amount. The Sequence Detection System 7700 ABI PRISM (produced and distributed by Perkin Elmer) can work both as a DNA amplifier and a collector of fluorescence signals from samples during the PCR reaction. These signals are then processed by a software capable of extrapolating the starting DNA amount in the analyzed samples by a standard curve built with the fluorescence signals from samples with known DNA content. It must be noted that such a system is endowed with two specificity levels: the specific annealing of the primers and the specific annealing of the probe.

SUMMARY OF THE INVENTION

A method generally applicable to the nucleic acid quantitation techniques based on the polymerase and 5' nuclease activity of nucleic acid polymerases, improving the efficiency of the techniques themselves, along with an enhanced sensitivity, accuracy and precision and a reduced measure variability, has now been found.

The method of the invention is based on the use of a calibrator during the steps of extraction of the sample, of target nucleic acid amplification and subsequent detection with suitable probes able to differentially hybridize to the calibrator and the target sequence.

The method of the invention can be applied to any absolute quantitation of nucleic acids from different biological sources, for example to the quantitation of viral or bacterial pathogens in body liquids (liquor, urine, plasma, serum, synovial fluid) or to the quantitation of environmental or food contaminants.

DETAILED DESCRIPTION OF THE INVENTION

Nucleic acid quantitation techniques, using the polymerase and 5' nuclease activity of the nucleic acid polymerases, rely on the extraction of nucleic acid from the sample, on the preparation of a reaction mix containing a polymerase, primers specific for the target sequence and a probe specific for a target sequence included between the regions complementary to the two primers, said probe being labeled with a reporter (this reporter being preferably a fluorochrome) and a quencher, followed by determination of the signal from the reporter label released when the polymerase contacts the 5' end of the probe annealed to the target nucleic acid.

According to the method of the invention, a known amount of the template nucleic acid, hereafter referred to as calibrator, is added to the sample before the extraction of the nucleic acid to be quantitatively detected (target nucleic acid). The calibrator has a sequence identical to the target nucleic acid sequence with the exception of one or more regions whose sequence is different from the corresponding regions of the target nucleic acid, having with respect to the latter a randomized sequence and a similar Tm. More specifically, one of those different regions must be the region complementary to the probe, with a Tm comprised in the range of ±4° C. the Tm of the target nucleic acid, preferably in the range ±2. The other different regions of the calibrator may be those annealing with the primers, which have randomized sequences with respect to the target nucleic acid and a Tm comprised in the range of ±1° C. the Tm of the target nucleic acid.

When this second embodiment is provided, i.e. when the calibrator regions complementary to the primers are varied with respect to the target nucleic acid, in addition to the regions complementary to the probe, it is possible to extremely reduce the competition events occurring between the target template and the calibrator, and to simultaneously measure the target template and the calibrator in a single reaction tube.

After extraction, the primers, and separately the probes derivatized with a reporter and a quencher, where the reporter can be equal or different among different probes, are added to the extracted sample-calibrator mixture. Two or more primers may be added to the reaction mixture, depending on the number of variable regions present on the calibrator annealing with the primers. Preferably, up to 3 pairs, more preferably up to two pairs of primers (forward and reverse) are used. Furthermore a thermostable polymerase with 5'-3' nuclease activity is added, thus starting the polymerase/nuclease reaction.

The reaction is carried out in a Sequence Detection System 7700 ABI PRISM that can work both as a DNA amplifier and a collector of fluorescence signals emitted from the reporter markers released upon polymerase nuclease activity. Virtually, three reactions are carried out in parallel, one of them in the presence of target nucleic acid specific probe, one in the presence of the calibrator specific probe/primers, and one in the presence of both.

The reaction in the presence of the target nucleic acid specific probe permits quantitation of the copy number of the extracted target nucleic acid ($N_o$). The reaction in the presence of the calibrator permits quantitation of the calibrator copy number recovered upon extraction ($C_o$). The reaction in the presence of both permits calculation of the total number of target templates and calibrator (T).

It is thus possible to calculate the percentage of the calibrator recovery yield R:

$$R=C_0/C,$$

from which the calibration factor (cal)

$$cal=1/R$$

and thus the actual number of nucleic acid units in the sample before extraction are obtained:

$$N=N_o \times Cal$$

The relation $$T=N_o+C_o$$

assures that the amplification efficiency of the standard and calibrator DNA remain identical.

The calibrator non-amplification makes it possible to detect any false negatives (technical errors; or presence of inhibitors), which represent one of the most important drawbacks when using amplification methods in clinical diagnostics.

The reaction conditions are the same as those commonly adopted in qcPCR reactions (Petrik j. et al., J. Virol. Methods, 64:147–159, 1997). The reaction conditions can be modified in order to compensate for the competition events, more exactly the primer concentration, the polymerase enzyme concentration, the annealing/extension time, or the concentration of cofactors such as $MgCl_2$ can be modified.

The target nucleic acid can be DNA or RNA, preferably DNA, while primers and probes are preferably deoxyribonucleotide sequences. When the nucleic acid is RNA a previous retro-transcription step is required in order to obtain the corresponding DNA. The probes include a fluorescent reporter label and a quencher label to reduce or to avoid fluorescence from the reporter label when the probes are free in solution.

TET (tetrachloro-6-carboxy-fluorescein), JOE (2,7-dimethoxy-4,5-dichloro-6-carboxyfluorescein), HEX (hexachloro-6-carboxy-fluorescein) are examples of reporter, preferably TAMRA (6-carboxy-tetramethyl-rhodamine) and FAM (6-carboxy-fluorescein) are used as quencher and reporter, respectively.

Preferably the 5' end of said probes is in the range of 1 to 30 nucleotides from the 3' end of the forward primer, i.e. at a distance to permit the reporter label release in the absence of nucleic acid polymerization. Preferably, the probes have a blocked 3' end in order to prevent the extension by polymerase, have a Tm higher than the primer Tm, and comprise 18 to 30 nucleotides.

The nucleic acid polymerase is a thermostable polymerase with 5'-3' nuclease activity, preferably a DNA polymerase, and more preferably a DNA polymerase derived from the Thermus species.

A great advantage of the described method is represented by the possibility to detect samples containing inhibitors and to mathematically characterize the yield of genetic material extraction. A further advantage is represented by the possibility of simultaneously measuring the calibrator and the target nucleic acid in the same reaction tube. The possibility of detecting total inhibitors of amplification reaction from the samples allows the elimination of false negatives often occurring with known techniques. Moreover, the calibration does not necessitate further standardization which is conversely required, for example, by the TaqMan technique (see Chatellard P. et al., J. Virol. Methods, 71:137–146, 1998).

The present invention also provides a kit to perform the above described method, including, depending on the target nucleic acid, a suitable calibrator, a probe specific for the target nucleic acid, two or more primers and a nucleic acid polymerase.

According to a preferred embodiment, the method of the invention is employed to quantitatively detect the genomic nucleic acid of the HHV-6, HHV-7, HHV-8, and HIV viruses, in a sample.

Particularly, in the case of HHV-6, the assay is divided into two steps: in the first step gene extraction is performed by a method based on the standard lysis-purification protocol by phenol-chloroform; in the second step the amplification reaction is carried out with specific primers and probes, selected by the "Primer Express" software (Perkin Elmer).

The primer and probe have been designed to amplify both type A and type B HHV-6 strains with the same efficiency. This feature is responsible for very high diagnostic sensitivity.

The calibration according to the method of the invention relies on adding to the sample, before DNA extraction, a known amount of a template DNA amplifiable with the same kinetic properties as the HHV-6 amplicon, but at the same time clearly distinguishable from it. A DNA fragment identical to that amplified by the HHV-6 primers, apart from the region complementary to the probe that has been modified so as to preserve the same nucleotide composition but with a random sequence, and with the same melting temperature (Tm), is thus cloned; the obtained plasmid, termed "calibrator", is amplified by the same primers and with the same kinetic as the standard plasmid, but it is revealed by the 7700 software only if the PCR mix contains a probe with a sequence complementary to the random sequence.

The calibrator plasmid is expanded and accurately quantitated by the spectrophotometer so as to add an exact amount of it to the samples to be extracted. Upon DNA extraction, samples thus contain a certain number of HHV-6 genomes and calibrator plasmid copies, dependent on the total yield of such an extraction; the HHV-6 DNA quantitation is thus possible, assuming such a yield to be identical for both the molecular species.

The reaction specific conditions are indicated in further detail in the example section.

To compensate for competition events, the reaction conditions were modified as follow: the primer concentration was elevated ten-fold, enzyme concentration was doubled, the amplification annealing/extension was increased by 8 seconds per cycle starting from the initial 60 seconds. However the competition events between templates narrowed the range of absolute quantitation (calibrated) from 7 to 5 order of magnitude, 2 above and 2 under the value of the calibrator input, while the relative quantitation range (non calibrated) and the ability to detect the experimental false negatives are unchanged.

According to an alternative embodiment, the original calibrator sequence has been further randomized in the two primers coding regions maintaining the theoretical Tm of the two original primers (as calculated by the specific software Primer Express PE foster city CA). The relevant sequences of the new calibrator molecules are reported in Table 2 of the examples. The target DNA molecule and the calibrator were amplified with the same kinetics, as evidenced by the following equations:

$y=37.804+-3.4402 \times LOG(x)$ R=1.000 for the standard template amplification, and $y=38.543+-3.568 \times LOG(x)$ R=0.998 for the calibrator template amplification.

The two molecules added in the same tube were correctly co-amplified, using standard PCR reactions, for more than 7 order of magnitude with no necessity to compensate for competitive events. In order to carry out the simultaneous detection and quantification of target DNA and calibrator in a single tube the calibrator was derivatized at the 5' end with VIC (Pe Biosystem), a fluorescent molecule having an emission spectrum different from the one used for the target DNA molecule detection.

To eliminate the interference generated by the partial overlapping of the emission spectra of the two dyes, the calibrator PCR conditions were modified by reducing the primers and probe concentrations (final concentration 50 nM for both). The reduction of the emission signal of VIC reporter was achieved without modification of the Ct (Cycle threshold) value, thus allowing a reproducible quantitation of the calibrator itself.

The spectral interference was completely avoided by adding the calibrator in a fixed concentration one log higher than the maximal amount of standard used in the reference curve (i.e. 10,000,000 copies of calibrator for a standard curve in which the highest concentration of standard was 1,000,000 copies reaction).

The following examples illustrate the invention in further detail.

EXAMPLES

Example 1

Selection of the HHV-6, HHV-7, HHV-8, HIV 35s CAMV and Mycobacterial sequences.

The U67 HHV-6 region (A variant, GeneBank Accession N°. X83413) and the 26 HHV-8 orf region (Chang et al., Science 266, 1865–1869, 1994) the HHV-7 region (Gene Bank AF037218), 35sCAMV (Gene Bank AF140604), RegX-SenX (Gene Bank MTY 13628) and 156110 (Gene Bank X17848), and the HIV region mapping between the LTR and gag region from nucleotide 684 to 810 using the sequence HXB2CG-Accession number K03455 (Gene Bank) are reported in Table 1 (primers and probe of the target nucleic acid and calibrator probe). The HHV-6 sequences (primers and probe for the target, calibrator's primers and probe) are reported in Table 2.

The probe sequences of the calibrators (HHV-7, HHV-8, HIV-1, CAMV, Myc. T.) and the calibrator's primers (HHV-6) were designed randomizing the probe region of the standard, while maintaining:
1. the same base composition (G+C/A+T) of the standard
2. an identical Tm (calculated by Perkin Elmer software)
3. an identical length (in order to have the same amplification efficiency)
4. and being characterized by an absolute absence of homology with the standard (target) in order to avoid cross-hybridization and interferences.

TABLE 1

| | Primers | Probes |
|---|---|---|
| HHV-7 | Forward (SEQ ID NO:1) | Standard (SEQ ID NO:3) |
| | 5' AGCGGTACCTGTAAAATCATCCA 3' | 5' ACCAGTGAGAACATCGCTCTAACTGGATCA 3' |
| | Reverse (SEQ ID NO:2) | Calibrator (SEQ ID NO:4) |
| | 5' AACAGAAACGCCACCTCGAT 3' | 5' TAAGCCCTGACCGCACGGGTATAATACTAA 3' |
| HHV-8 | Forward (SEQ ID NO:5) | Standard (SEQ ID NO:7) |
| | 5' GTCCAGACGATATGTGCGC 3' | 5' CATTGGTGGTATATAGATCAAGTTCCGCCA 3' |
| | Reverse (SEQ ID NO:6) | Calibrator (SEQ ID NO:8) |
| | 5' ACTCCAAAATATCGGCCGG 3' | 5' ACTATTCCATGCGGAATTCGAGCATAGTTG 3' |
| HIV-1 | Forward (SEQ ID NO:9) | Standard (SEQ ID NO:11) |
| | 5' TACTGACGCTCTCGCACC 3' | 5' ATCTCTCTCCTTCTAGCCTCCGCTAGTCAA 3' |
| | Reverse (SEQ ID NO:10) | Calibrator (SEQ ID NO:12) |
| | 5' TCTCGACGCAGGACTCG 3' | 5' ACTCTCAGCGGCATTCTCCTCACTTCTACT 3' |
| CAMV | Forward (SEQ ID NO:13) | Standard (SEQ ID NO:15) |
| | 5' GTCTTGCGAAGGATAGTGGGA 3' | 5' TGCGTCATCCCTTACGTCAGTGGAGAT 3' |
| | Reverse (SEQ ID NO:14) | Calibrator (SEQ ID NO:16) |
| | 5' CACGTCTTCAAAGCAAGTGGA 3' | 5' ATCGCTACATGCTAGGCATCTGTGTGC 3' |
| Myc. T. 1 | Forward (SEQ ID NO:17) | Standard (SEQ ID NO:19) |
| | 5' AGGAGGAGTGGCGCTGATG 3' | 5' ACGAGGAGTCGCTGGCCGATCC 3' |
| | Reverse (SEQ ID NO:18) | Calibrator (SEQ ID NO:20) |
| | 5' ACTCGGCGAGAGCTGCC 3' | 5' TCCAGCGTCAGGCGTAGGCAGC 3' |

TABLE 1-continued

| | Primers | Probes |
|---|---|---|
| Myc. T. 2 | Forward (SEQ ID NO:21)<br>5' AGGCGAACCCTGCCCAG 3'<br>Reverse (SEQ ID NO:22)<br>5' GATCGCTGATCCGGCCA 3' | Standard (SEQ ID NO:23)<br>5' TCGACACATAGGTGAGGTCTGCTACCCACA 3'<br>Calibrator (SEQ ID NO:24)<br>5' ACTACGACTACGGCTGCGATCGACATCGAT 3' |

TABLE 2

| | Primers | Probes |
|---|---|---|
| HHV-6 | Forward (SEQ ID NO: 25)<br>5' CAAAGCCAAATTATCCAGAGCG 3'<br>Reverse (SEQ ID NO: 26)<br>5' CGCTAGGTTGAGGATGATCGA 3' | Standard (SEQ ID NO: 27)<br>5' CACCAGACGTCACACCCGAAGGAAT 3'<br>Calibrator (SEQ ID NO: 28)<br>5' TACGCAACGCCAACAGACCTAGCGA 3'<br>Calibrator |
| | Primer forward (SEQ ID NO: 29)<br>5' CCGGAAACCGAACATTACTGAA 3'<br>Primer reverse (SEQ ID NO: 30)<br>5' TTACGTGAGGATGATCGAGGC 3' | Probe (SEQ ID NO: 31)<br>5' TACGCAACGCCAACAGACCTAGCGA 3' |

Example 2

HHV-6 Standard (target nucleic acid) and Calibrator cloning and preparation.

The fragments used for the standard and calibrator DNA construction in the HHV-6 virus detection system are schematically represented in FIG. 1 (1-A and 1-B respectively).

The Standard fragment sequence was obtained by amplification of the viral DNA from HHV-6 GS strain and subsequent cloning into pCRII plasmid vector (Invitrogen). The calibrator fragment (133 bp) was chemically synthesized by an Oligosynthetizer (Perkin Elmer), and then cloned in the same vector as above.

After cloning, both fragments were completely sequenced in order to identify: i) the identity (co-linearity) of the standard fragment with the original viral DNA, ii) the identity of the calibrator fragment with the artificially designed sequence.

As shown in FIG. 1 the arrows, oriented in the transcription direction, indicate the oligonucleotide sequence employed as primers. The dotted line identifies in both constructs the regions of 25 nucleotide used as the probes (lowercase) differentiating the two constructs, otherwise identical in the remaining 108 nucleotides. These regions, even though they have the same base composition and a very similar Tm, were designed in such a way as to function as a heterologous system, allowing avoidance or minimization of the cross-hybridization events between the probes employed in the specific fluorimetric detection and the standard and calibrator fragments.

Example 3

HHV-6 calibrator/standard system validation

Absence of cross-hybridization

We thus experimentally verified the absence of spurious signals from cross-hybridization. Increasing concentrations of the standard and calibrator fragment (from 101 to 106 plasmid copies per PCR reaction) were measured using the homologue probe (standard probe for the standard DNA, calibrator probe for the calibrator DNA) or the heterologous probe (standard probe for the calibrator DNA, calibrator probe for the standard DNA). FIG. 2B shows the detection of the various template amounts employing the probe homologous to the fragment to measure, where: a) indicates the standard amplification curve and, b) the calibrator curve. Detection takes place for both constructs with overlapping kinetics (curves 1–5, a, b) furthermore indicating that the template amplification is proportional to the measured fluorescence signal. The use of heterologous probe (FIG. 2A) for both templates does not generate a signal appreciably higher than the system background noise.

Co-linearity

Amplification co-linearity of the two templates was measured by comparing the two regression line equations generated from the values obtained as threshold cycles as a function of the increasing copy number of the employed template.

The resulting equations are:

$y=37.804+-3.4402 \times LOG(x)$ R 1.000 for the standard template amplification $y=38.543+-3.568 \times LOG(x)$ R=0.998 for the calibrator template amplification.

The slope ratio of the two lines is 1.017 thus indicating that the two systems are perfectly overlapping both as amplification efficiency and as fluorimetric detection dynamics.

Calibration range

Figure 3:
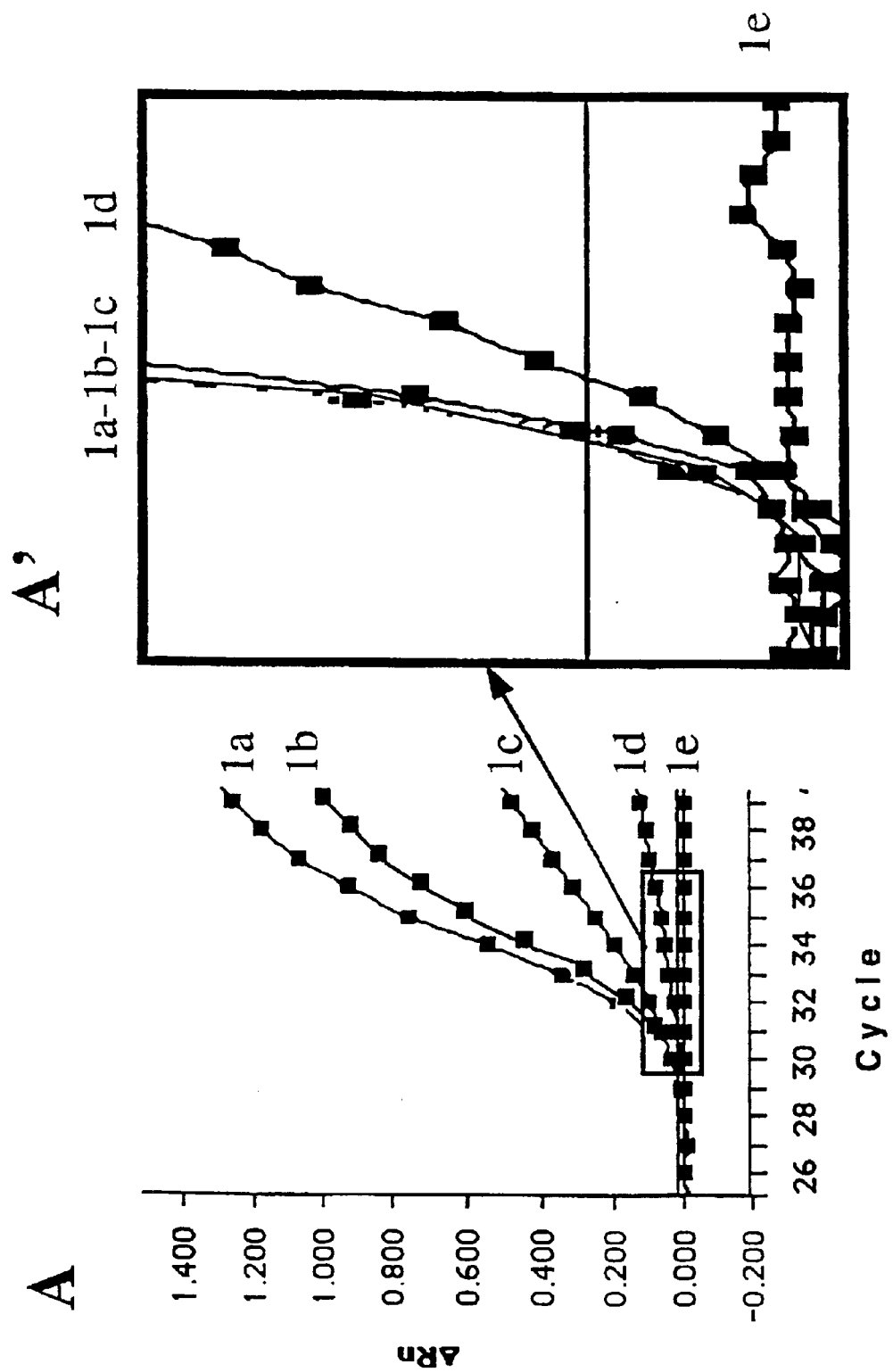
Figure 3:
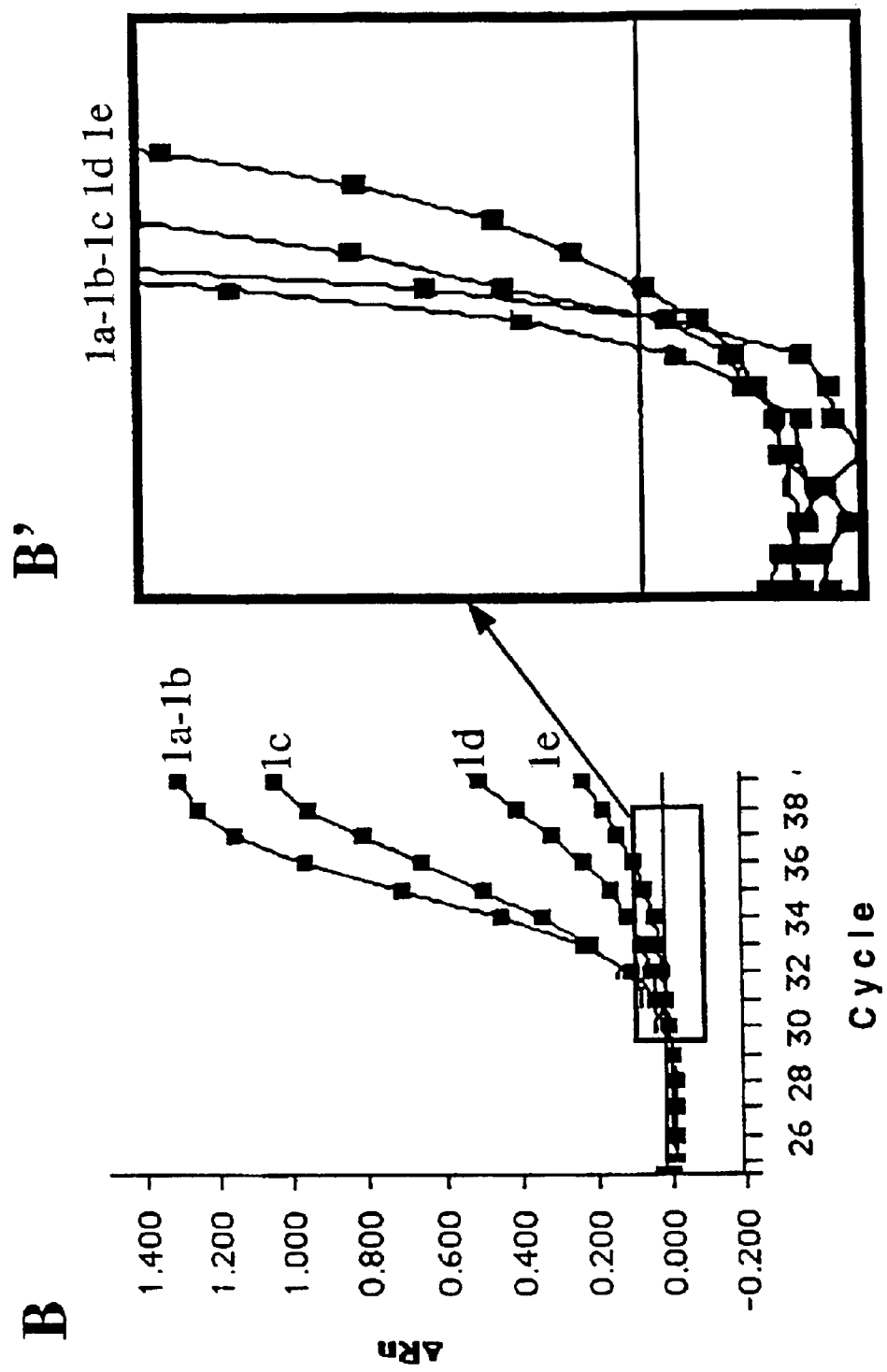

Amplification of the two templates in the same PCR reaction causes an appreciable modification of the amplification curve detected by the system (FIG. 3A). In fact it is possible that for increasing copy amounts, i.e. 500 calibrator copies in unique dose co-amplified in the presence of 0, 500, 5,000, 50,000, 500,000 standard copies (from 1a–1e respectively), the fluorescent signal is changed both in the accumulation kinetic and in the final amount of the released product. At the threshold cycle (A' insert), standard template concentrations equivalent to or higher by a Log (A' insert—1a–1c curves) do not influence the accuracy of the calibrator quantitation. For higher concentrations (1d, 1e curves) the quantitation is partially (marked delay of the threshold cycle, 1d) or completely impaired (1e). The optimization of: the PCR conditions, and particularly the combined actions of primer concentration increase (from 300 nM to 3 μM), doubling the enzyme concentration (from 0.625 to 1.25 AmpliTaq Gold units), and the increase in length of every PCR cycle (8 sec. increment per cycle during the annealing and extension steps), cause an improvement of the amplified product accumulation kinetic and of the final yield of the fluorescence signal FIG. 3B, curves 1a–1e). At the threshold cycle (B' insert), standard template concentrations up to 2 Log (50,000 copies) higher than the calibrator input, do not modify its quantitation (B' curves 1e–1d). For higher concentrations (500,000 copies) the fluorimetric signal from the calibrator probe is measurable, although the lack of signal exponential increase does not allow maintenance of an accurate measure of the calibrator (B' curve 1e).

Figure 4:
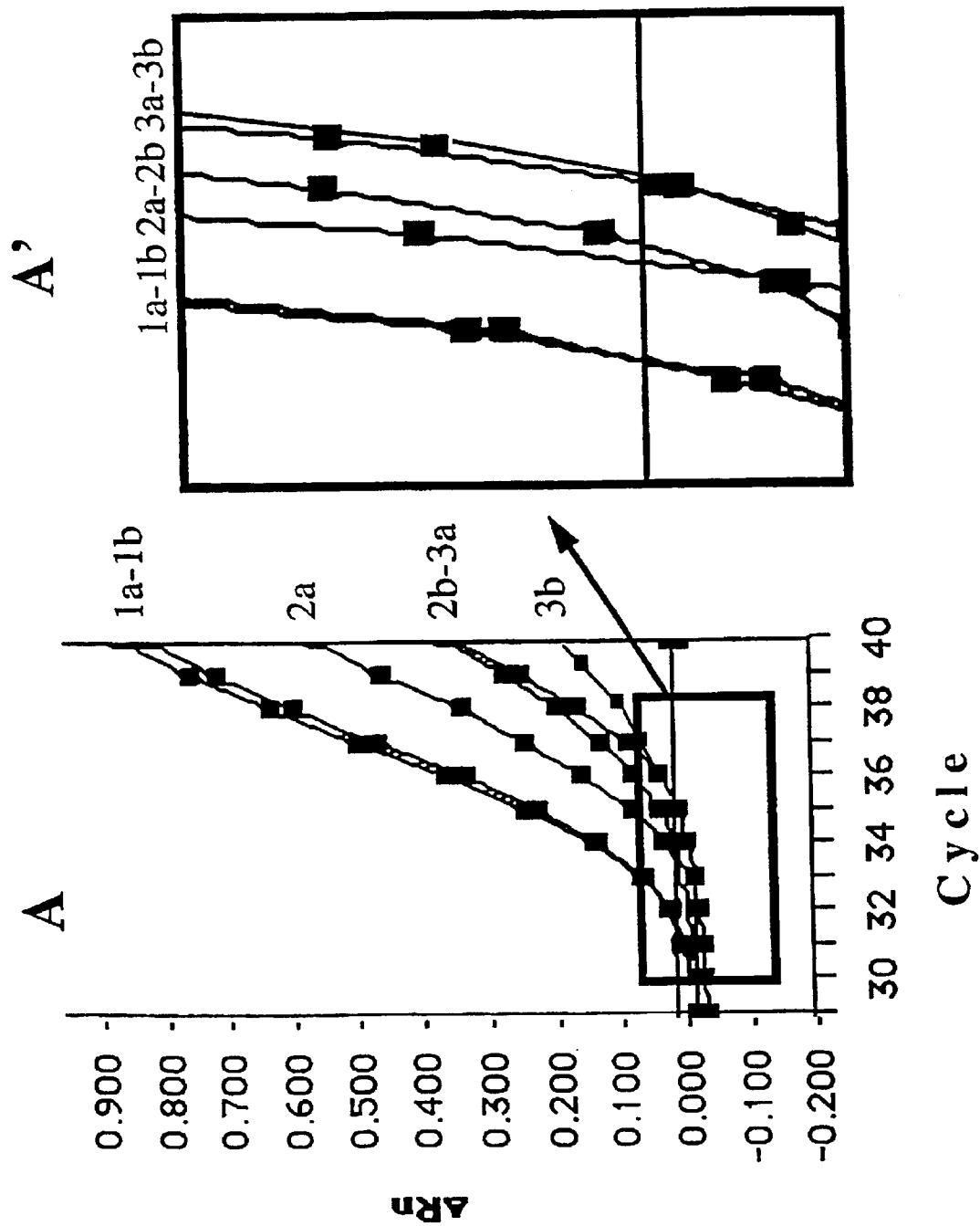

In opposite conditions (FIG. 4A), i. e. with excess of calibrator up to 2 Log concentration with respect to the standard, (e. g. 500 copies of calibrator vs. 5 copies of standard), the analysis of the reaction kinetics is as above. In particular, in optimized conditions, the quantitation at the threshold cycle (A' insert; "a" indicates the amplification curve of the standard in the absence of the calibrator, "b" the curve measured in the presence of the calibrator), in this case of the standard, is not modified (A' curves 1a–1b: 100 copies of standard and 25 copies of standard concentration, 3a–b:5 copies of standard concentration).

By means of this optimization it can thus be obtained an accurate quantitation of a template whose amount is unknown, with the following practical advantages:
1) Absolute control (both qualitative and quantitative) of the whole process of sample purification and amplification with a dynamic range of at least 5 Log (e. g. 5 to 50,000 copies per reaction);
2) Quantitative control of purification and amplification process with a dynamic range of at least 7 logarithms (false negatives due to technical error or to the presence of contaminants inhibiting the PCR reaction).
3) Eliminating the unknown sample serial dilution;
4) Inserting only one known dose of the calibrator (e. g. 500 copies).

What is claimed is:

1. A method for the quantitative detection of a target nucleic acid sequence of a HHV-8, from a sample, which comprise a the following steps:

a) extraction of the nucleic acid from the sample with another nucleic acid (calibrator) previously added to the sample, said calibrator having i) the same sequence of the target nucleic acid, apart from the region hybridizing to a target probe, which is randomized with respect to the corresponding region of the target nucleic acid, maintaining the same nucleotide composition, and ii) a Tm equal to the target nucleic acid Tm +/−4° C. with respect to the corresponding region of the target nucleic acid, having the same nucleotide composition, but with a random sequence, and a similar Tm, b) mixing the extracted target nucleic acid and calibrator with a forward primer which has the sequence of SEQ ID NO5, with a reverse primer which has the sequence of SEQ ID NO:6, with said target probe bearing a reporter and a quencher, said target probe having the sequence SEO ID NO:7, and a calibrator probe bearing a reporter and a quencher, said calibrator probe having a sequence of SEQ ID NO:8, and annealing said forward primer, said reverse primer and said probes bearing a reporter and a quencher to the target nucleic aid and to the corresponding randomized region on the calibrator, in the presence of nucleic acid polymerase with 5'–3' nuclease activity, under conditions to carry out a polymerization reaction, and c) determination of the signal associated with the reporters released due to the 5' polymerase nuclease activity.

2. A method for the quantitative detection of a target nucleic acid sequence of a HHV-8, from a sample, which comprises the following steps:

a) extraction of the nucleic acid from the sample with another nucleic acid (calibrator) previously added to the sample, said calibrator having i) the same sequence as the target nucleic acid, apart from the regions hybridizing to a probe or to the primers, which are randomized with respect to the corresponding regions of the target nucleic acid, maintaining the same nucleotide composition, and ii) a Tm equal to the target nucleic acid Tm +/−4° C.

b) mixing the extracted target nucleic acid and calibrator a forward primer which has the sequence of SEO ID NO:5, with a reverse primer which has the sequence of SEQ ID NO:6, with a probe bearing a reporter and a quencher, said target probe having the sequence of SEQ ID NO.7, and a calibrator probe bearing a reporter and a quencher, said calibrator probe having a sequence of SEQ ID NO:8, and annealing said forward primer, said reverse primer, and said probes bearing a reporter and a quencher to the target nucleic acid and to the corresponding randomized region on the calibrator, in the presence of nucleic acid polymerase with 5'–3' nuclease activity, under conditions to carry out a polymerization reaction, and c) determination of the signal associated with the reporters released due to the 5' polymerase nuclease activity.

3. Method according to the claim 1, wherein the calibrator Tm is comprised in the ±4° C. range of the target nucleic acid Tm.

4. Method according to claim 1 wherein the 5' end of the probes is 1 to 30 nucleotides from the 3' end of the forward primer.

5. Method according to claim 1, wherein the probe is 3' end blocked in order to prevent the extension by the polymerase.

6. Method according to claim 1 wherein said nucleic acid polymerase is thermostable DNA polymerase with 5'–3' nuclease activity.

7. Method according to claim 1, wherein said probe includes a quencher label able to reduce or to avoid the reporter label fluorescence when the probe is free in solution.

* * * * *

SEQUENCE LISTING

<160> NUMBER OF SEQ ID NOS: 31

<210> SEQ ID NO 1
<211> LENGTH: 23
<212> TYPE: DNA
<213> ORGANISM: Human herpesvirus

<400> SEQUENCE: 1
agcggtacct gtaaaatcat cca                23

<210> SEQ ID NO 2
<211> LENGTH: 20
<212> TYPE: DNA
<213> ORGANISM: Human herpesvirus

<400> SEQUENCE: 2
aacagaaacg ccacctcgat                20

<210> SEQ ID NO 3
<211> LENGTH: 30
<212> TYPE: DNA
<213> ORGANISM: Human herpesvirus

<400> SEQUENCE: 3
accagtgaga acatcgctct aactggatca                30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Calibrator
      modified region

<400> SEQUENCE: 4
taagccctga ccgcacgggt ataatactaa                30

<210> SEQ ID NO 5
<211> LENGTH: 19
<212> TYPE: DNA
<213> ORGANISM: Human herpesvirus

<400> SEQUENCE: 5

```
gtccagacga tatgtgcgc                                                    19

<210> SEQ ID NO 6
<211> LENGTH: 19
<212> TYPE: DNA
<213> ORGANISM: Human herpesvirus

<400> SEQUENCE: 6
actccaaaat atcggccgg                                                    19

<210> SEQ ID NO 7
<211> LENGTH: 30
<212> TYPE: DNA
<213> ORGANISM: Human herpesvirus

<400> SEQUENCE: 7
cattggtggt atatagatca agttccgcca                                        30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Calibrator
      modified region

<400> SEQUENCE: 8
actattccat gcggaattcg agcatagttg                                        30

<210> SEQ ID NO 9
<211> LENGTH: 18
<212> TYPE: DNA
<213> ORGANISM: Human immunodeficiency virus

<400> SEQUENCE: 9
tactgacgct ctcgcacc                                                     18

<210> SEQ ID NO 10
<211> LENGTH: 17
<212> TYPE: DNA
<213> ORGANISM: Human immunodeficiency virus

<400> SEQUENCE: 10
tctcgacgca ggactcg                                                      17

<210> SEQ ID NO 11
<211> LENGTH: 30
<212> TYPE: DNA
<213> ORGANISM: Human immunodeficiency virus

<400> SEQUENCE: 11
atctctctcc ttctagcctc cgctagtcaa                                        30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Calibrator
      modified region

<400> SEQUENCE: 12
actctcagcg gcattctcct cacttctact                                        30
```

-continued

<210> SEQ ID NO 13
<211> LENGTH: 21
<212> TYPE: DNA
<213> ORGANISM: Cauliflower mosaic virus

<400> SEQUENCE: 13
gtcttgcgaa ggatagtggg a                                             21

<210> SEQ ID NO 14
<211> LENGTH: 21
<212> TYPE: DNA
<213> ORGANISM: Cauliflower mosaic virus

<400> SEQUENCE: 14
cacgtcttca aagcaagtgg a                                             21

<210> SEQ ID NO 15
<211> LENGTH: 27
<212> TYPE: DNA
<213> ORGANISM: Cauliflower mosaic virus

<400> SEQUENCE: 15
tgcgtcatcc cttacgtcag tggagat                                       27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Calibrator
      modified region

<400> SEQUENCE: 16
atcgctacat gctaggcatc tgtgtgc                                       27

<210> SEQ ID NO 17
<211> LENGTH: 19
<212> TYPE: DNA
<213> ORGANISM: Mycobacterium tuberculosis

<400> SEQUENCE: 17
aggaggagtg gcgctgatg                                                19

<210> SEQ ID NO 18
<211> LENGTH: 17
<212> TYPE: DNA
<213> ORGANISM: Mycobacterium tuberculosis

<400> SEQUENCE: 18
actcggcgag agctgcc                                                  17

<210> SEQ ID NO 19
<211> LENGTH: 22
<212> TYPE: DNA
<213> ORGANISM: Mycobacterium tuberculosis

<400> SEQUENCE: 19
acgaggagtc gctggccgat cc                                            22

<210> SEQ ID NO 20
<211> LENGTH: 22
<212> TYPE: DNA
<213> ORGANISM: Artificial Sequence
<220> FEATURE:

```
<223> OTHER INFORMATION: Description of Artificial Sequence: Calibrator
      modified region

<400> SEQUENCE: 20
tccagcgtca ggcgtaggca gc                                              22

<210> SEQ ID NO 21
<211> LENGTH: 17
<212> TYPE: DNA
<213> ORGANISM: Mycobacterium tuberculosis

<400> SEQUENCE: 21
aggcgaaccc tgcccag                                                    17

<210> SEQ ID NO 22
<211> LENGTH: 17
<212> TYPE: DNA
<213> ORGANISM: Mycobacterium tuberculosis

<400> SEQUENCE: 22
gatcgctgat ccggcca                                                    17

<210> SEQ ID NO 23
<211> LENGTH: 30
<212> TYPE: DNA
<213> ORGANISM: Mycobacterium tuberculosis

<400> SEQUENCE: 23
tcgacacata ggtgaggtct gctacccaca                                      30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Calibrator
      modified region

<400> SEQUENCE: 24
actacgacta cggctgcgat cgacatcgat                                      30

<210> SEQ ID NO 25
<211> LENGTH: 22
<212> TYPE: DNA
<213> ORGANISM: Human herpesvirus

<400> SEQUENCE: 25
caaagccaaa ttatccagag cg                                              22

<210> SEQ ID NO 26
<211> LENGTH: 21
<212> TYPE: DNA
<213> ORGANISM: Human herpesvirus

<400> SEQUENCE: 26
cgctaggttg aggatgatcg a                                               21

<210> SEQ ID NO 27
<211> LENGTH: 25
<212> TYPE: DNA
<213> ORGANISM: Human herpesvirus

<400> SEQUENCE: 27
caccagacgt cacacccgaa ggaat                                           25
```

```
<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Calibrator
      modified region

<400> SEQUENCE: 28
tacgcaacgc caacagacct agcga                                              25

<210> SEQ ID NO 29
<211> LENGTH: 22
<212> TYPE: DNA
<213> ORGANISM: Human herpesvirus

<400> SEQUENCE: 29
ccggaaaccg aacattactg aa                                                 22

<210> SEQ ID NO 30
<211> LENGTH: 21
<212> TYPE: DNA
<213> ORGANISM: Human herpesvirus

<400> SEQUENCE: 30
ttacgtgagg atgatcgagg c                                                  21

<210> SEQ ID NO 31
<211> LENGTH: 25
<212> TYPE: DNA
<213> ORGANISM: Human herpesvirus

<400> SEQUENCE: 31
tacgcaacgc caacagacct agcga                                              25
```